US00PP29112P3

(12) United States Plant Patent
Tesselaar

(10) Patent No.: US PP29,112 P3
(45) Date of Patent: Mar. 13, 2018

(54) ***AGAPANTHUS* PLANT NAMED 'ATISEA'**

(50) Latin Name: ***Agapanthus praecox* subspecies *orientalis***
Varietal Denomination: ATIsea

(71) Applicant: Anthony Tesselaar, Silvan (AU)

(72) Inventor: Anthony Tesselaar, Silvan (AU)

( * ) Notice: Subject to any disclaimer, the term of this patent is extended or adjusted under 35 U.S.C. 154(b) by 13 days.

(21) Appl. No.: 14/999,562

(22) Filed: May 26, 2016

(65) Prior Publication Data

US 2017/0347516 P1 Nov. 30, 2017

(51) Int. Cl.
*A01H 5/02* (2006.01)

(52) U.S. Cl.
USPC ..... Plt./398
CPC ..... *A01H 5/02* (2013.01)

(58) Field of Classification Search
USPC ..... Plt./398
See application file for complete search history.

*Primary Examiner* — Susan McCormick Ewoldt
(74) *Attorney, Agent, or Firm* — Cassandra Bright

(57) ABSTRACT

A new and distinct *Agapanthus* cultivar named 'ATIsea' is disclosed, characterized by abundant production of flowering umbels on short plants. Flowers are dark blue. Plants are uniquely tolerant of both drought and damp conditions. The new variety is a *Agapanthus*, typically produced as an outdoor ornamental plant.

3 Drawing Sheets

Latin name of the genus and species: *Agapanthus praecox* subspecies *orientalis*.

Variety denomination: 'ATIsea'.

BACKGROUND OF THE INVENTION

The new cultivar is the product of chance discovery. The new variety originated as a naturally occurring mutation of the patented variety of *Agapanthus* 'ATIblu', U.S. Plant Pat. No. 14,332.

The new variety was discovered by the inventor, Anthony Tesselaar, during 2010 in an outdoor planting of the parent variety in a commercial nursery in Silvan, Australia. After identifying the new variety as a potentially interesting selection, the inventor continued confidential observation of 'ATIsea, finally selecting the variety for further propagation during 2011.

Asexual reproduction of the new cultivar 'ATIsea' was first performed by division in Silvan, Australia December 2011, on a very limited basis. Access to all plants was restricted, as plants were kept in a location not open to the public. Through subsequent propagation, multiple generations have been reproduced, which have shown that the unique features of this cultivar are stable and reproduced true to type.

SUMMARY OF THE INVENTION

The cultivar 'ATIsea' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ATIsea.' These characteristics in combination distinguish 'ATIsea' as a new and distinct *Agapanthus* cultivar:

1. Dark blue flowers.
2. Abundant inflorescence production, many flowering scapes per plant.
3. Short plant stature.
4. Tolerance for both drought and damp conditions.

PARENT COMPARISON

Plants of the new cultivar 'ATIsea' are similar to the parent, *Agapanthus* 'ATIblu' in most horticultural characteristics. The new variety, however, has darker blue flowers than the parent variety.

COMMERCIAL COMPARISON

Plants of the new cultivar 'ATIsea' are similar to the commercial variety *Agapanthus* 'Storm Cloud', unpatented. The new variety differs from 'Storm Cloud in the following characteristics:

1. The new variety produces more flowering scapes then 'Storm Cloud'.
2. The new variety tolerates wet conditions better than 'Storm Cloud'.
3. Plants of the new variety are shorter and more compact than plants of 'Storm Cloud'.

BRIEF DESCRIPTION OF THE PHOTOGRAPHS

The accompanying photograph in FIG. 1 illustrates in full color a mass planting of 'ATIsea' grown in Silvan, Australia.

DETAILED BOTANICAL DESCRIPTION

Figure 1:
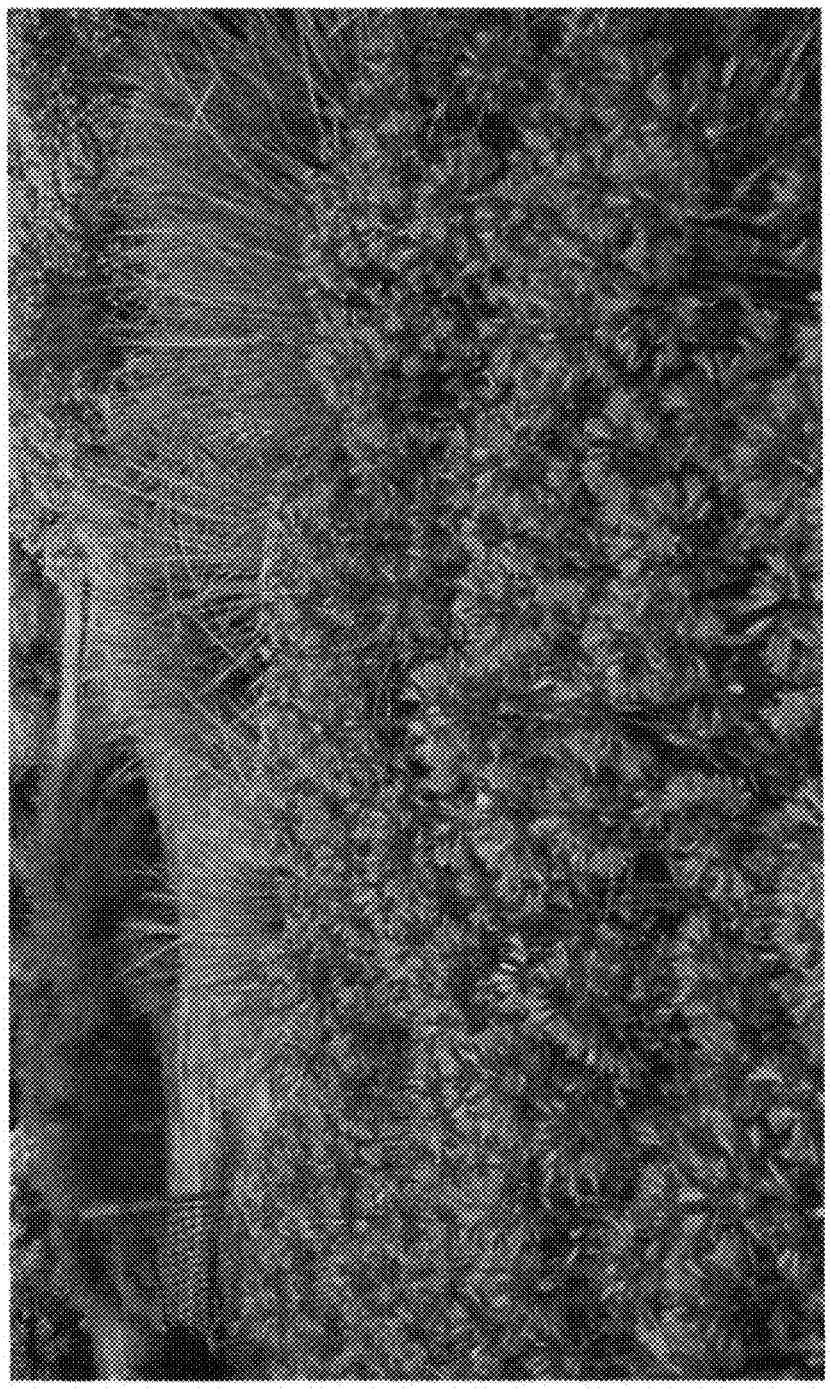
Figure 2:
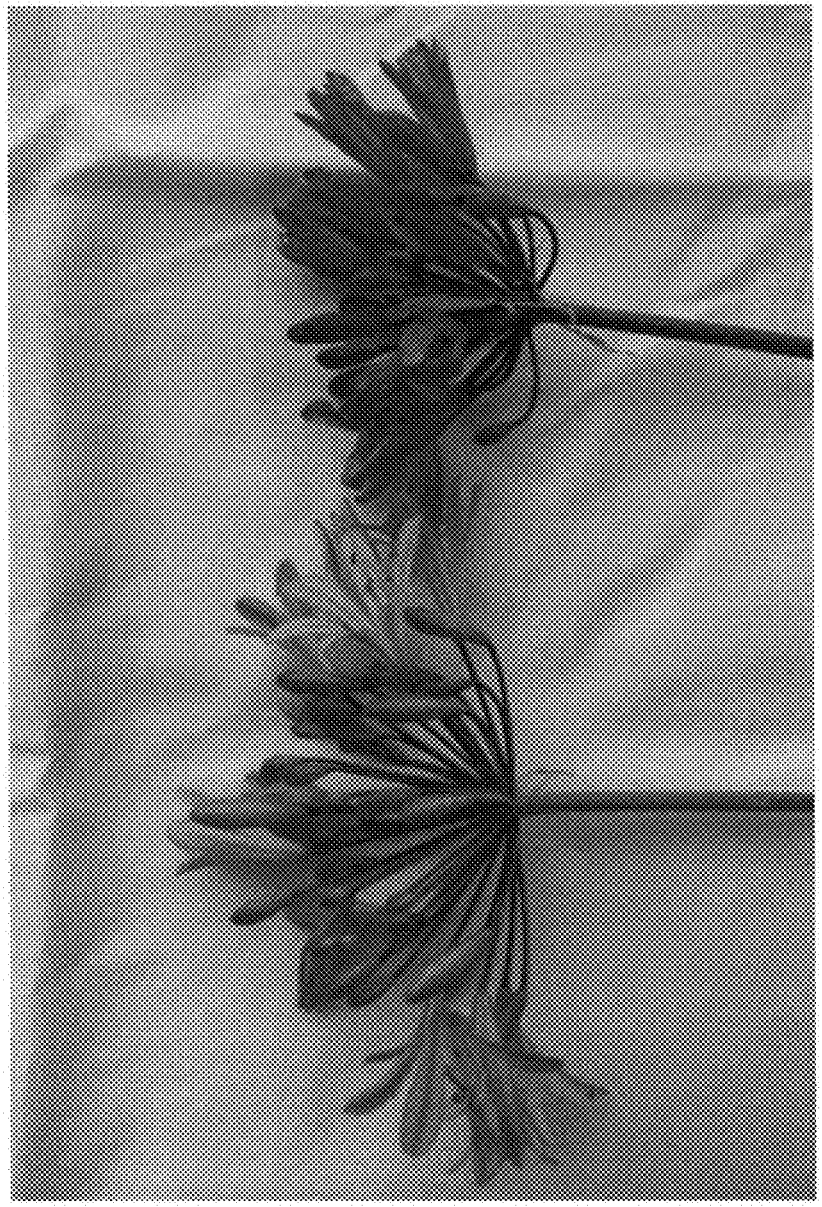
FIG. 2 illustrates in full color a close up of the flowers of 'ATIsea' and the parent variety 'ATIblu'. Flowers of 'ATIsea' are the darker umbel on the right.
Figure 3:
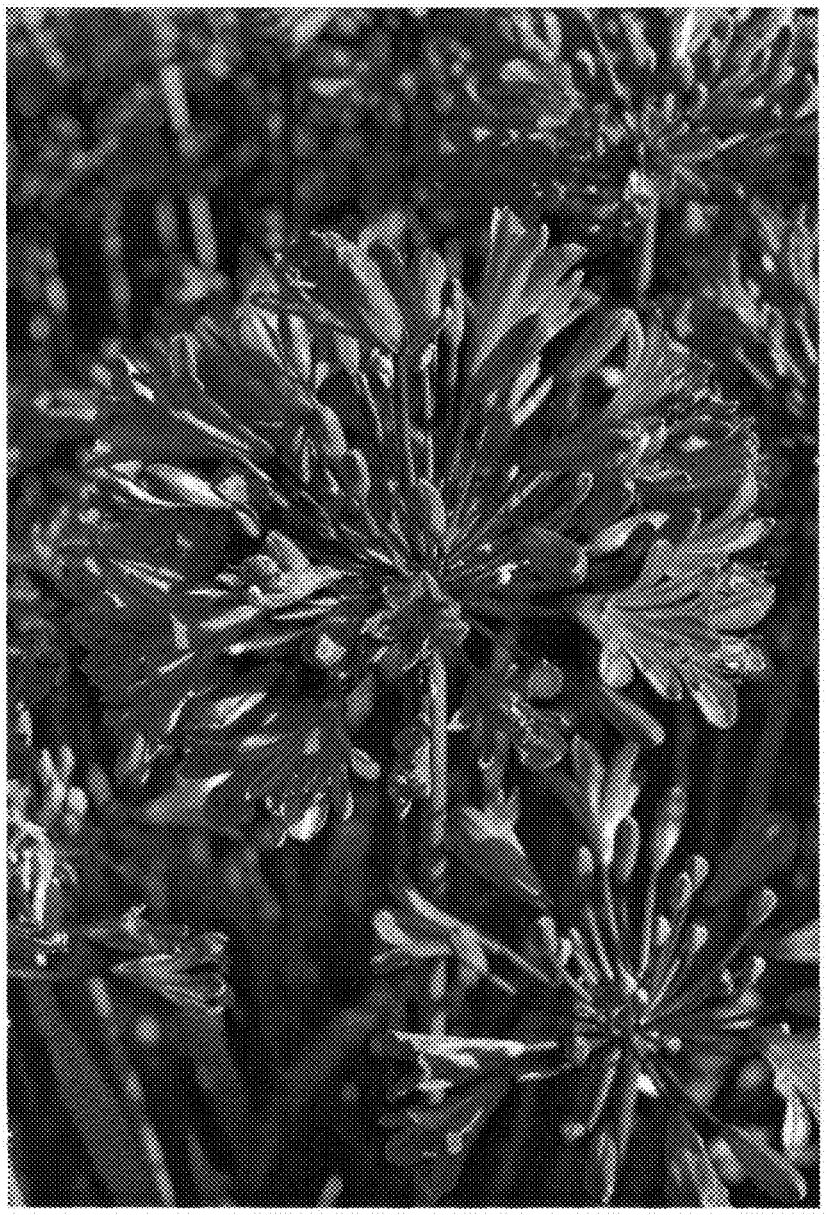
FIG. 3 illustrates a close up of a flowering umbel of the new variety. The photographs were taken using conventional techniques and although colors may appear different from actual colors due to light reflectance it is as accurate as possible by conventional photographic techniques.

In the following description, color references are made to The Royal Horticultural Society Colour Chart 2007, except where general terms of ordinary dictionary significance are used. The following observations and measurements describe 'ATIsea' plants grown outdoors in Silvan, Australia. Plants are approximately 1 year old. Temperatures ranged from approximately 8° C. to 15° C. at night and 10° C. to 32° C. during the day. No artificial light, photoperiodic treatments were given to the plants. No chemical treatments were given to plants. Measurements and numerical values represent averages of typical plant types.

Botanical classification: *Agapanthus praecox* subsp. *orientalis 'ATIsea'*.

PROPAGATION

Root description: Thick, fleshy root system colored near Brown 199D and N199B.

PLANT

Growth habit: Clump forming tender perennial with arching, pendulous foliage.

Height: Flowering plane 700 to 850 mm.

Plant spread: Approximately 800 mm.

Growth rate: Rapid.

Stem: No stem, basal clump.

Growth pattern: The plant makes growth throughout most of the year but particularly in the Spring and Summer months. This growth is in the form of basal shoots or pups as well as some leaf extension.

FOLIAGE

Leaf:

*Average leaf length*.—Approximately 230 mm.

*Average leaf width*.—Approximately 12 mm.

*Quantity*.—Approximately 30 to 50 per mature plant.

*Shape*.—Linear.

*Texture*.—Glabrous, smooth, without ridges, upper and lower surfaces.

*Apex*.—Broad acute.

*Base*.—Truncate.

*Margin*.—Entire.

*Color*.—Coloration for both upper and lower surfaces. Immature: Near RHS Green 137B. Mature: Near RHS Green 137B.

*Venation*.—Type: Linear. Venation color upper side: Indistinguishable from leaf blade. Venation color under side: Indistinguishable from leaf blade.

FLOWER

Natural flowering season: Spring and Summer. Heavy flowering Spring and until mid-Summer. Sporadic flowering from mid-Summer until Fall.

Length of flowering period: Approximately 120 days.

Inflorescence type: Terminal Umbel with approximately 35 to 40 individual flowers.

Individual flower type: Single.

Flower profile: Funnelform.

Lasting quality: Inflorescence shows no significant signs of aging for approximately 8 weeks.

Bud:

*Flower bud diameter*.—Approximately 1 cm.

*Shape*.–Ovate.

*Color*.—Near RHS Violet-Blue N89C.

Inflorescence:

*Diameter*.—150 mm.

*Stem length*.—Approximate average 700 mm.

Individual flowers:

*Length*.—Average 3.0 cm.

*Width*.—Average 2.5 cm.

Tepals:

*Arrangement*.—Rotate, overlapping.

*Length*.—Average 28 to 30 mm.

*Width*.—Average 8 to 10 mm.

*Quantity*.—6.

*Tepal lobe*.—Length: Average 18 mm. Width: Average 8 to 10 mm. Shape: Linear. Margin: Entire. Base: Fused. Apex: Mucronate, or rounded.

*Perianth tube*.—Length: Approximately 8 mm. Color: Inner surface: Near Violet-Blue 94D. Outer surface: Near Violet-Blue 96C.

Flower color:

*When opening*.—Inner surface: Near RHS Violet-Blue 94C. Outer surface: Near RHS Violet-Blue 96B, apex slightly flushed Violet-Blue 90C.

*Fully opened*.—Inner surface: Near RHS Violet-Blue 94D. Outer surface: Near RHS Violet-Blue 96C.

*Fading*.—Inner surface: Near RHS Violet-Blue 97C. Outer surface: Near RHS Violet-Blue 96C.

Flower filament color: Near Violet-Blue 94D.

Flower anther color: Near Purple 79A.

Anther quantity: 6, each approximately 25 mm long.

Stamen protrusion: Protrudes very slightly past the floral lobe apex.

Pistil:

*Number*.—1.

*Length*.—Approximately 2.7 cm.

*Style color*.—Near RHS Violet 88C.

*Stigma*.—Shape: Linear. Color: Near RHS Violet 88A.

Pedicel:

*Length*.—30 mm.

*Texture*.—Glabrous.

*Color*.—Near Green 137B, sometimes lightly flushed Violet 86B.

Fragrance: None.

OTHER CHARACTERISTICS

Seed production: Seed vessels: approximately 10 mm long, 3 mm diameter. Colored near Yellow-Green N144D. 3 flat sides, 3 separate compartments. Moderate seed production. Seeds oblong, flat, approximately 2 mm long, colored near Black 202A.

Disease resistance: Neither resistance nor susceptibility to normal diseases and pests of *Agapanthus* have been observed.

Temperature tolerance: USDA zones 8 through 11.

Drought tolerance: Will tolerate considerable dryness once established. Plants are also tolerant of damp conditions.

What is claimed is:

1. A new and distinct cultivar of *Agapanthus* plant named 'ATIsea' as herein illustrated and described.

* * * * *